(12) United States Patent
Simmons, Sr.

(10) Patent No.: US 6,393,609 B1
(45) Date of Patent: May 28, 2002

(54) PROTECTIVE SIDESHIELD REMOVABLY ATTACHABLE TO AN EYEGLASS FRAME

(75) Inventor: Bennie F. Simmons, Sr., Lewisville, TX (US)

(73) Assignee: Safety Optical Service, Lewisville, TX (US)

( * ) Notice: Subject to any disclaimer, the term of this patent is extended or adjusted under 35 U.S.C. 154(b) by 0 days.

(21) Appl. No.: 09/870,079

(22) Filed: May 30, 2001

(51) Int. Cl.[7] .................................................. A61F 9/04
(52) U.S. Cl. .................................................. 2/13; 2/449
(58) Field of Search ............................... 2/13, 12, 449, 2/448, 451; 351/44, 47, 158

(56) References Cited

U.S. PATENT DOCUMENTS 5,394,567 A * 3/1995 Vatterott ........................ 2/449
5,748,278 A    5/1998 Simmons
6,007,196 A * 12/1999 Saba et al. ..................... 351/44

* cited by examiner

*Primary Examiner*—Peter Nerbun
(74) *Attorney, Agent, or Firm*—Jones, Day, Reavis & Pogue (57) ABSTRACT

A shield for removable attachment to an eyeglass frame front having a pair of eyeglass lens holding frames and a pair of pivotal temples for holding said eyeglass lens frames on the head of a user to provide protection on the top, the bottom and the side of the eye. The sideshields are attached to the eyeglass lens holding frames in a detachable manner and are mounted such that they do not interfere with movement of the eyeglass temples so that the temples can be folded or, if they are spring-pivoted temples, can move outwardly a predetermined distance without substantial interference by the sideshields.

24 Claims, 6 Drawing Sheets

PROTECTIVE SIDESHIELD REMOVABLY ATTACHABLE TO AN EYEGLASS FRAME

BACKGROUND OF THE INVENTION

1. Field of the Invention

The present invention relates in general to safety glasses which provide protection to the eyes and, in particular, to a full sideshield for a removable attachment to an eyeglass frame without interfering with movement of the eyeglass temples.

2. Description of Related Art Including Information Disclosed Under 37 C.R.F. §§1.97 and 198

Safety glasses are well known in the prior art and are used to protect the eyes of an individual from airborne particles, high-velocity projectiles, wind, and the like. As used herein, and by those skilled in the art, the terms "safety glasses" or "eyeshields" typically mean a protective barrier in front of the eye. A "sideshield," on the other hand, typically means a protective barrier to the side, above or below the eye and normally supplements safety glasses.

There are many different types of sideshields that are used with eyeglass frames. For example, some are permanently attached to the eyeglass frames and provide reasonable protection for the top, side, and bottom of the eye. Sideshields providing such protection and which also fit a broad range of eyeglass frame shapes and sizes are known as universal sideshields. Further, an eyeglass frame, as used herein, is intended to include the front portion and temples or bows.

One such type of universal sideshield is of plastic construction having a side flap, partial top and bottom flaps, front flaps extending from each of the side and top portions, and bottom flaps extending from each of the side and top portions that fold around the front edge of the eyeglass frame. The temple of the eyeglass frame on each side is inserted through appropriate slots formed in the side portion of the sideshield so that the sideshield can slide on the temple toward the eyeglass front and be held in place by the temple. In such case, when the temples are folded, the sideshields move with the temples and thus are subject to repositioning themselves on the temples and requiring a readjustment each time the temples are folded and then unfolded.

Another type of sideshield includes substantially a clear side portion with a perpendicularly-extending top portion and a small perpendicularly-extending front portion that engages the front portion of the eyeglass frame. There is a resilient continuous elastic band that passes through four orifices in the side to enable the temples to slide under two spaced portions of the continuous elastic band to hold the sideshield to the temple of the glasses. Again, each time the temples are folded, the sideshield moves with the temples thus causing readjustment to be necessary each time the temples are folded and unfolded. Also, this sideshield provides very little protection for the top of the eye and none from the bottom.

A third type of universal sideshield is attached to the temple portion of the frame using a screw and nut that clamps the sideshield to the temple when tightened.

Another type of universal sideshield is formed of an injection molded flat part having four slots at different points through which the temple of the eyeglass frame can be threaded and attempt to adjust for pantoscopic angle variations.

Thus, these examples of prior art sideshields are attached to the temples and move with the temples except those which are permanently attached to the eyeglass front.

Further, each of the prior art detachable sideshields has a fixed pantoscopic angle (the angle the temple makes with the eyeglass front to which it is attached) molded into them that cannot be easily varied for eyeglasses with a different pantoscopic angle.

It would be desirable to have a full sideshield to provide substantial protection for the eye from the top, side, and bottom and which would fit a broader range of eyeglass frames than most sideshields, and which is not affected by the pantoscopic angle of the eyeglass frame.

SUMMARY OF THE INVENTION

The present invention provides full sideshields for removable attachment to an eyeglass frame without interfering with movement of the temples attached by hinges to the eyeglass frame. The sideshield is typically formed from a polycarbonate which may be transparent, absorptive or opaque and is generally arcuate-shaped having a periphery for generally conforming to the shape of the eyeglass frame and has a top portion, a bottom portion, and a side portion integrally formed as a single unit. A flange portion extends inwardly from at least one of the top, bottom or side portions of the sideshield in front of and substantially parallel to the eyeglass frame. An elastomeric member attaches the sideshield to the eyeglass frame without interfering with movement of the temples.

Thus, the present invention relates to a full sideshield to provide protection to the eye and which is removable attached to each side of an eyeglass frame having a pair of lens and a pair of pivotable temples attached to the eyeglass frame by hinges for holding the eyeglass frames on the head of the user.

As will be understood by those skilled in the art, eyeglass hinges include a portion mounted to the front frame of the eyeglasses referred to as the "frame front hinge" and a portion mounted to a temple referred to as the "temple hinge." The sideshield comprises a generally arcuate-shaped shield removably attached to each frame front in a fixed relationship and having a periphery generally conforming to the frame front. Each sideshield has a side portion integrally formed at a first edge to a top portion, and integrally formed at a second edge to a bottom portion for protecting the eyes of the user. A detachable elastomeric member releasably engages both the sideshield and a portion of the eyeglass frame between the lens holder and the hinge commonly referred to as the "end piece" or at the "frame front itself to removably attach the sideshield to the lens frame in a fixed relationship without interfering with pivotal movement of the temples.

First and second spaced slots having a selected width are formed in the side portion, each extending from first and second enlarged slots in front of the sideshield along the first and second edges to enlarged areas which are also located toward the front of the sideshield. Third and fourth slots are formed in the rear portion of the sideshield and define a tab member.

An elastomeric member having a relaxed diameter greater than the width of the spaced slots is deformed to pass through the slots into the enlarged areas. The elastomeric member engages the end piece of the frame of the eyeglasses between the lens holder and the hinge or the frame front hinge itself and extends into the enlarged areas of the first and second spaced slots and along the first and second edges of the side portion into third and fourth spaced slots and then passes under the tab member.

BRIEF DESCRIPTION OF THE DRAWINGS

These and other features of the present invention will be more fully disclosed when taken in conjunction with the following DESCRIPTION OF SELECTIVE EMBODIMENTS in which like numerals represent like elements and in which.

DETAILED DESCRIPTION OF THE EMBODIMENTS

Figure 1:
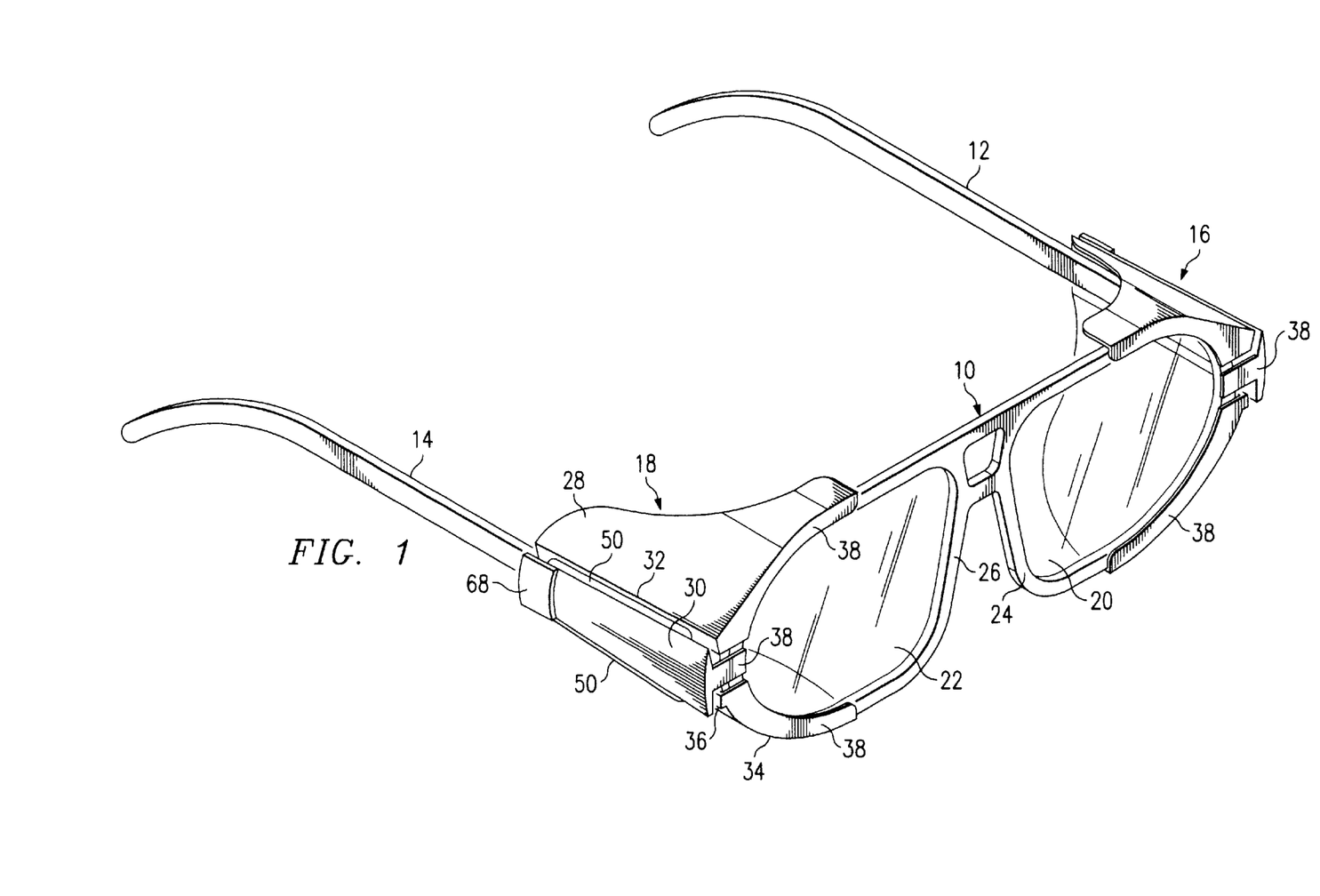
FIG. 1 is a partial isometric view of a pair of eyeglass frames and temples having the novel sideshields of the present invention attached thereto.

FIG. 1 is a partial isometric view of a pair of eyeglasses having the novel full sideshields removably attached to each side thereof. As can be seen in FIG. 1, the eyeglass frame front portion 10 has temples 12 and 14 pivotally attached to each side thereof for holding the eyeglass frame front 10 on the face of a user. The novel full sideshields 16 and 18 are removably attached on each side of the frame front 10 and form a semicircle around the eyeglass lens 20 and 22 in front of the eye cavity of the user to provide eye protection on the top, bottom and side of the eye. Each sideshield 16 and 18 is a generally arcuate-shaped sideshield having a periphery for generally conforming to the shape of the individual eyeglass lens holders 24 and 26. Each of the novel sideshields 16 and 18 has a top portion 28 integrally formed to a side portion 30, along a first edge 32, and a bottom portion 34 integrally formed with side portion 30 at a second edge 36. It can be further seen from FIG. 1 that the sideshields fitting each side of the eyeglass frame are mirror images of each other.

As shown, a first flange portion 38 extends from at least one of the top portion 28, side portion 30, and bottom portion 34 at least partially in front of and substantially parallel to the eyeglass lens holder 26. Also, according to one embodiment, a second flange portion 40 also extends inwardly from at least one of the top and bottom portions behind and substantially parallel to the eyeglass lens holder 26 to secure the eyeglass lens holder 26 between the first and second flange portions 38 and 40. It will be noted that in the illustrative embodiment, the first flange portion 38 extends inwardly along the front portion 42 of the lens holder 26 while the second flange portion 40 extends behind and substantially parallel to the rear portion 44 of the individual eyeglass lens holder 26, thus retaining the eyeglass lens holder 26 between the first and second flange portions 38 and 40. This is shown clearly in FIGS. 2 and 3.

Figure 2:
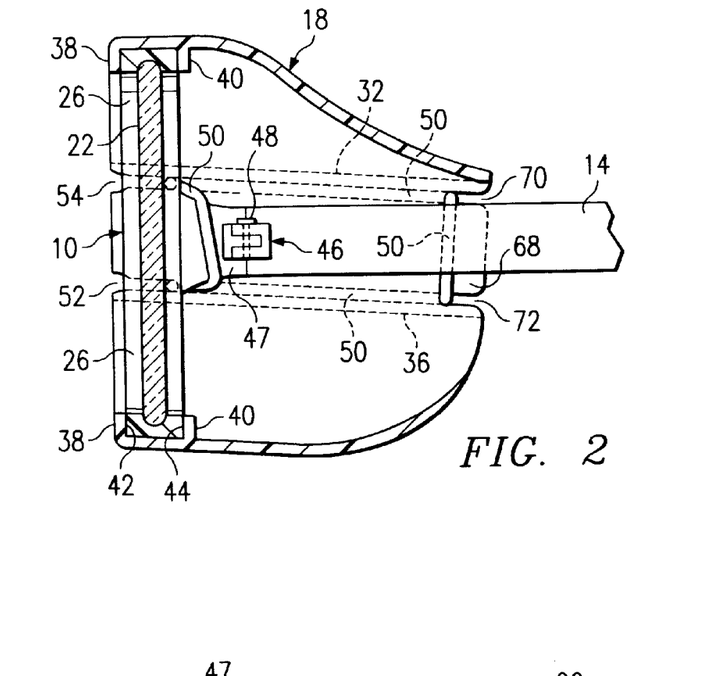
FIG. 2 is a cross-sectional inside view of sideshield attached to the rearwardly extending end piece of the eyeglass frame forward of the hinge, and with one of the temples extending outwardly from the end piece.

Continuing with FIG. 2, it can be seen that with most eyeglass frames 10, temple 14 is attached by a hinge 46 to a portion 47 of each side of the individual eyeglass lens holders 24 and 26 for holding the eyeglass frame 10 on the head of the user. The portion 47 of the eyeglass frame to which the hinge is attached is typically referred to by those skilled in the art as the "end piece." The temple 14 is pivotally attached to the frame 10 by hinge 46 at pivot point 48, as is well known in the art.

Further, as will be appreciated by those skilled in the art, each hinge 46 will include a first portion secured or mounted to the end piece 47 of the eyeglass frame 10 located between the side of the lens holder and the hinge 46. This first portion of the hinge is referred to herein as the frame front hinge portion 51 or simply the "frame front hinge." Hinge 46 will also include a second portion 53 secured or mounted to the temple 14 and is hereinafter referred to as the temple hinge portion or simply "temple hinge."

Figure 4:
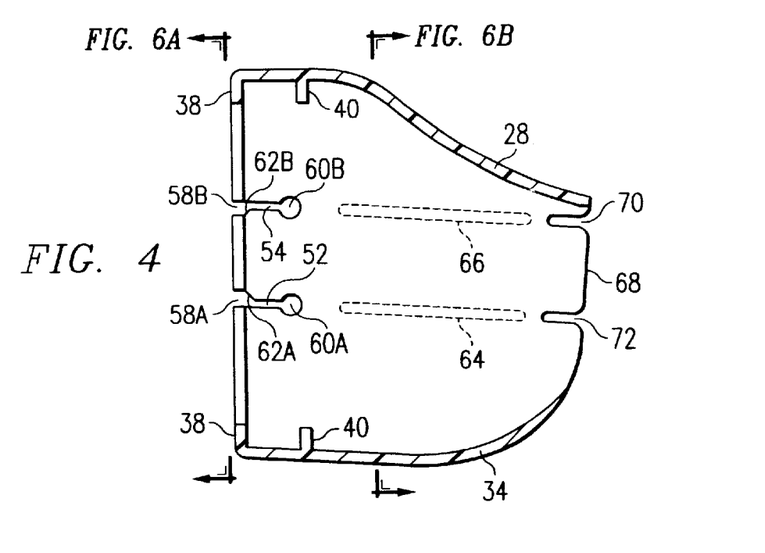
FIG. 4 is a side view facing the inside of the novel eyeglass sideshield of the present invention illustrating points along which cross-sectional views are shown.

Note also in the illustrated embodiment of FIG. 4 that the first flange portion 38 of the shield 10, according to the embodiment of FIG. 2, extends partially in front of the eyeglass lens holder 26 at 42 along substantially the entire periphery of the sideshield except for the enlarged slots 58A and 58B of slots 52 and 54. Also note in FIG. 4 that the second flange portion 40 extends only from the top and bottom portions of the sideshield 18 behind the eyeglass lens holder at 44 to secure the eyeglass frame between the first and second flange portions 38 and 40.

Figure 3A:
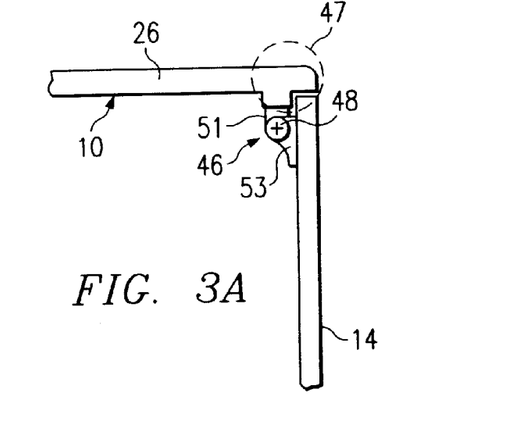
FIGS. 3A, 3B and 3C are top views of two types of typical eyeglass frames showing two types of end pieces and a hinge.
Figure 3B:
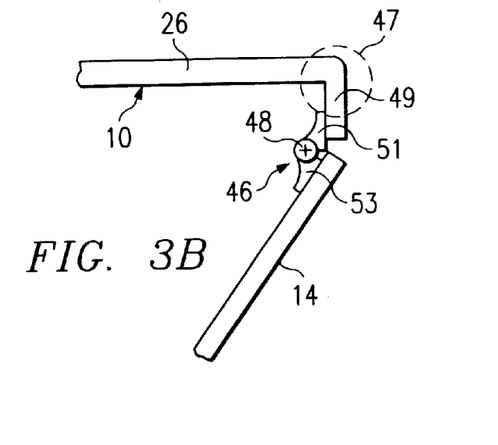
Figure 3C:
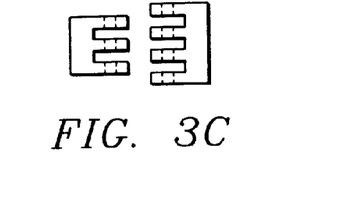

Referring now to FIG. 3A, there is shown a typical plastic frame having an end piece 47 with a very short or no rearward projection 49. FIG. 3B shows a typical metal frame (also some plastic frames) having an extending rearward projection 49. This type frame often uses a three-leaf hinge with two leaves attached to the frame 26 and a single leaf attached to the temple 14. FIG. 3C shows a rugged seven-leaf hinge (four leaves attached, for example, to the end piece 47 of the frame and three leaves attached to the temple 14).

The side view of FIG. 4 facing the inside of the sideshield shows the sideshield before being installed on a pair of eyeglasses and without the elastomeric member 50 being installed. As shown, the first and second slots 52 and 54 extend from first enlarged slots 58A and 58B in the front of the sideshield to enlarged areas 60A and 60B, respectively.

Figure 5A:
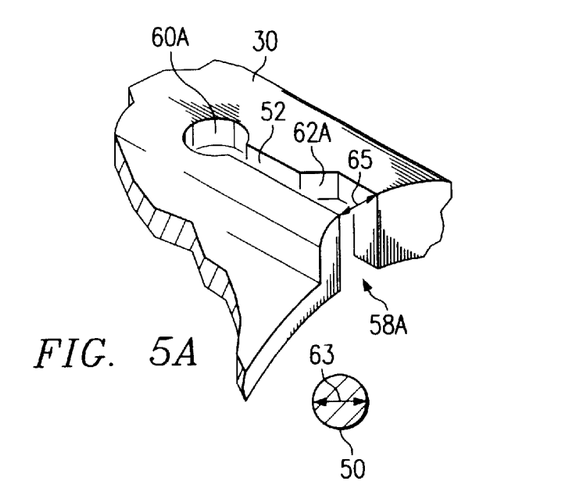
FIGS. 5A and 5B are enlarged perspective views of the front portion of the sideshield and one of the spaced slots illustrating the function of the enlarged slots.
Figure 5B:
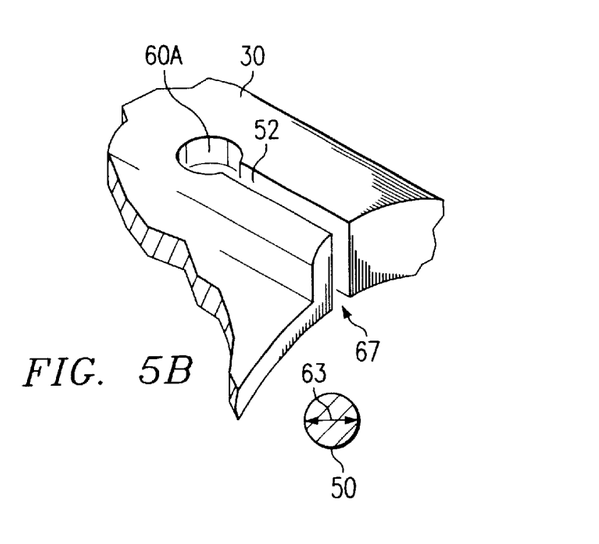

FIGS. 5A and 5B illustrate how the use of the enlarged slots 58A and 58B (shown in FIG. 5A) facilitate passing the elastomeric member 50 through the spaced slot 52 to the enlarged area 60A. In FIG. 5A, the diameter 63 of the elastomeric member 50 is seen to be approximately the same or slightly smaller than the width 65 of enlarged slot 58A. However, as shown in FIG. 5B, the diameter 63 of elastomeric member 50 is substantially greater than the width of slot 52 as shown at 67. Enlarged slot or area 58A provides an effective way for easily passing the elastomeric member 50 into enlarged area 60A while allowing the use of simple and inexpensive injection molding dies.

It should also be noted that, according to one embodiment, there is a sloping or tapered area 62A and 62B from the first enlarged areas 58A and 58B to their respective slots 52 and 54. However, the transition from the enlarged areas 60A and 60B to the respective slots 52 and 54 is abrupt. Although the actual dimension of the slots 52 and 54 and the enlarged areas 58A and 58B and 60A and 60B are not critical, the width of the slots 52 and 54 are selected to be somewhat less than the relaxed diameter of the elastomeric member 50. On the other hand, according to one embodiment, the dimension of the enlarged slots 58A and 58B and the enlarged areas 60A and 60B are selected to be approximately the same size as the elastomeric member 50. These enlarged openings may be slightly smaller than the relaxed diameter of the elastomeric member 50, but are preferably slightly larger. The arrangement of the enlarged slots 58A and 58B sloping to the spaced slots 52 and 54, as discussed above, allows for easily attaching the elastic or elastomeric member 50 to the sideshield thereby protecting it from being broken or abraded during the assembly process. This helps to prevent premature failures. However, the abrupt transition from enlarged areas 60A and 60B to narrow slots 52 and 54 provides a barrier against accidental removal of the elastomeric member 50. Again, it should be understood that the dimensions of the enlarged areas, the slots and the elastomeric member may vary for different applications or uses. However, if the elastomeric member 50 is selected to have a relaxed diameter of about 0.070 inches, it has been determined that selecting the enlarged slots 58A and 58B to be about 0.080 inches, the enlarged areas 60A and 60B to be 0.10 inches, and the spaced slots 52 and 54 to have a width of about 0.030 inches results in an exemplary sideshield.

Figure 6A:
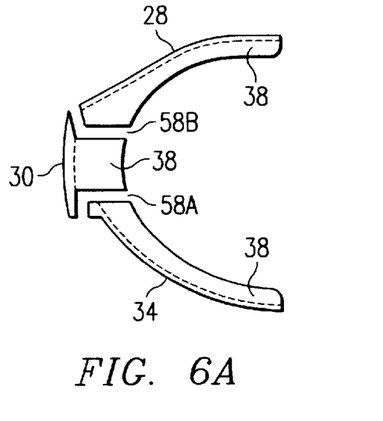
FIGS. 6A and 6B illustrate the cross-sectional views taken along the section lines shown in FIG. 4.
Figure 6B:
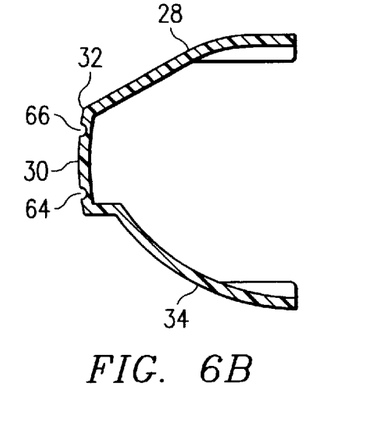

FIGS. 6A and 6B illustrate the cross-sectional views taken along the lines indicated in FIG. 3 and show the top portion 28, the side portion 30, the bottom portion 34, the slots 52 and 54, and the grooves 64 and 66.

Figure 7A:
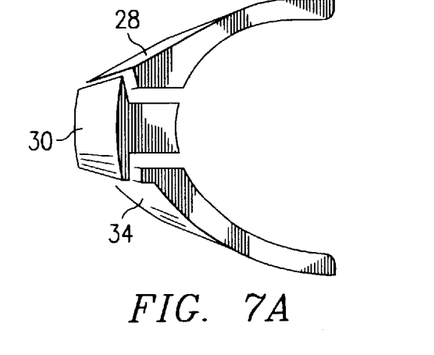
FIGS. 7A, 7B and 7C illustrate the use of living hinges to adjust the size of the sideshield to fit small, intermediate and large size eyeglass frames.
Figure 7B:
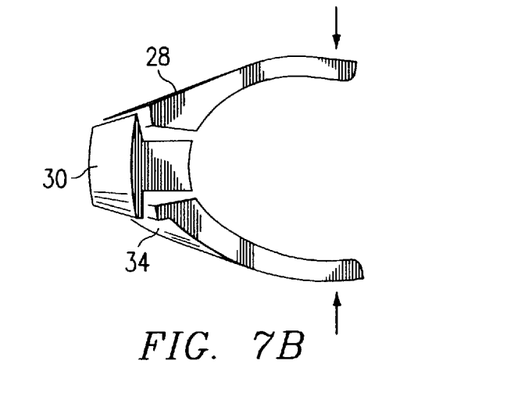
Figure 7C:
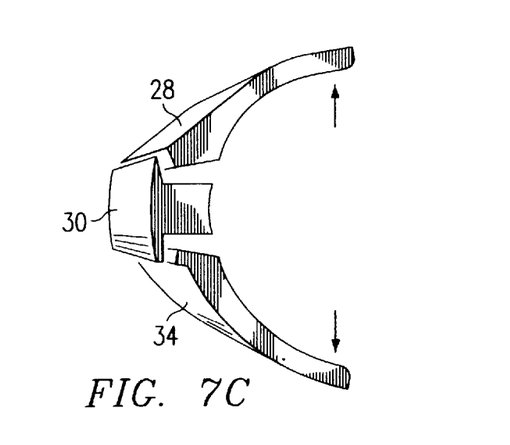

As can also be seen in FIG. 4 and the cross-sectional view of FIG. 6B, the present invention can further incorporate "living hinges" to permit the sideshield to be easily adjusted to accommodate eyeglass frames of various sizes. The perspective view of FIGS. 7A, 7B and 7C illustrate the sideshield of the present invention being adjusted for a normal eyeglass frame, a larger eyeglass frame and a smaller eyeglass frame, respectively.

The living hinge maintains its shape or position until intentionally readjusted, such as for example, to fit another eyeglass frame of a different size, and is formed by defining a pair of grooves 64 and 66 along or proximate the edges 36 and 34 which join the side portion 30 of the sideshield to the top portion 28 and the bottom portion 34, respectively. The exact dimension of the grooves 64 and 66 defined in the sideshield may vary depending upon the composition of the sideshield material and the nominal thickness of the sideshield.

According to one embodiment using a plastic material such as polycarbonate having a nominal thickness of about 0.050 inches, groove 64 was selected to be about 0.70 inches long. The thickness of the sideshield material at groove 64 was about 0.03+0.005−0.002 inches, and the thickness of the material for groove 66 was about 0.020+0.005−0.002 inches.

Figure 8:
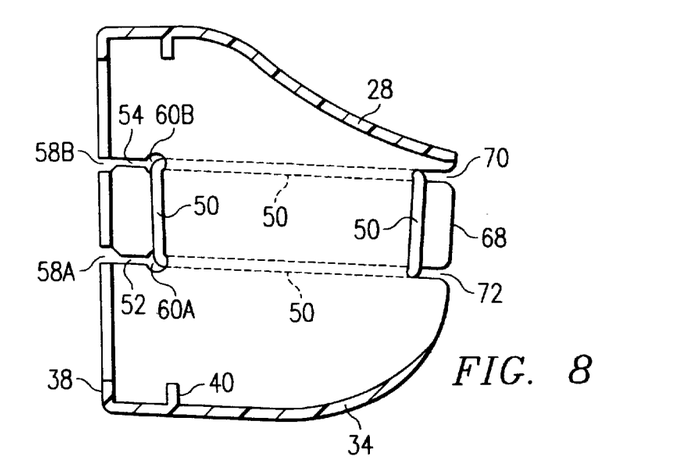
FIG. 8 is a side view of the sideshield similar to FIG. 4 and including a continuous elastic band to attach the sideshield to the eyeglass frame.
Figure 9:
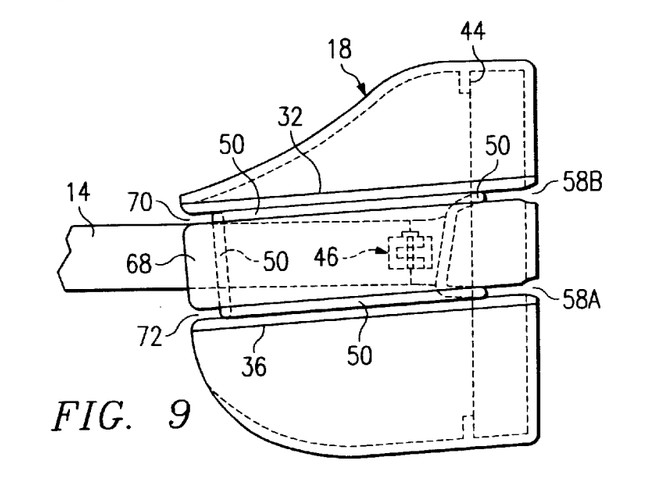
FIG. 9 is an outside side view of the sideshield showing a continuous elastic band in place to attach the sideshield to a portion or end piece of the eyeglass frame between the lens holder and the hinge.
Figure 10:
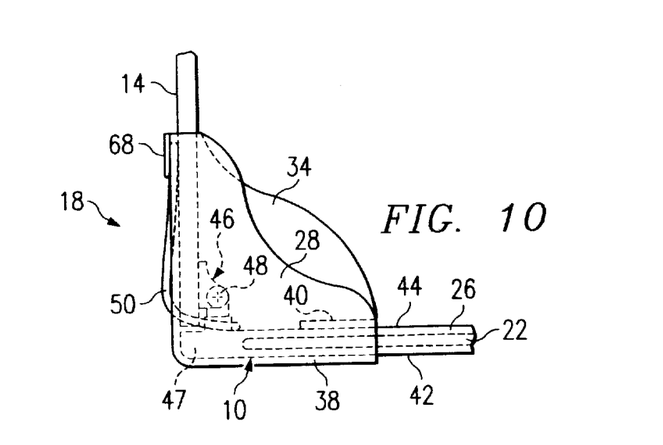
FIG. 10 is a top view of one of the novel sideshields of the present invention shown using a continuous elastic band to attach the sideshield to the eyeglass frame front.

FIGS. 2, 8, 9, 10 and 11 show embodiments of the present invention to hold the sideshield to the front portion of the eyeglass frame 10. According to this embodiment, the elastomeric member 50 is a continuous elastic band 56, such as, for example only, a rubber O-ring. The O-ring or continuous elastic band 56 engages end piece or portion 47 of the eyeglass frame 10 as shown in FIGS. 2 and 10, or at the frame front hinge portion 51 itself of hinge 46 as shown in FIGS. 8 and 9 and extends into the enlarged areas 60A and 60B of first and second spaced slots 52 and 54. The O-ring is stretched along corresponding ones of the first and second edges 32 and 36 into the third and fourth slots 70 and 72 and under the tab or flange 68. Thus, by stretching the continuous elastic band 56 to engage the third and fourth slots 70 and 72 under the sideshield tab 68, tension is applied to the eyeglass lens holder 26 and the sideshield 18 to fixedly hold the sideshield 18 to the eyeglass lens holder 26.

As was discussed, FIG. 4 is a side view of one of the sideshields 16 or 18 illustrating cross-sectional lines A—A and B—B associated with the shield. The cross sections are shown in FIGS. 6A and 6B. Note also that the sideshields 16 and 18 include a top portion 28, a side portion 30, and a bottom portion 34. As discussed above, slots 70 and 72 are formed at the rear of the sideshields 16 and 18 and define the tab or flange 68. The first groove 64 extends at least part way between enlarged area 60A and slot 72, and the second grove 66 extends at least part way between enlarged area 60B and 70.

Figure 11:
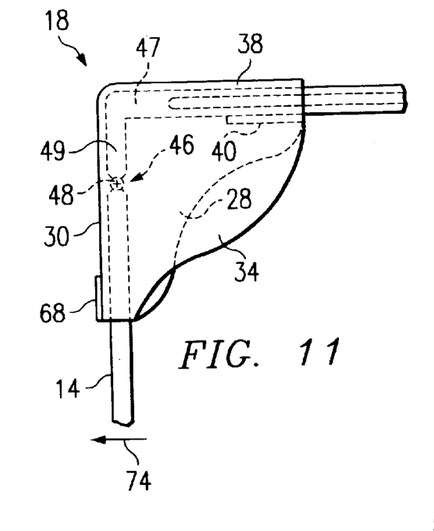
FIG. 11 is a bottom view of the novel sideshield of the present invention illustrating the eye protection received from the bottom of the eye and an end piece of the eyeglass frame with a rearwardly extending portion for attaching the temple.

FIG. 11 is a bottom view of the sideshield 18 attached to an eyeglass frame having an extended portion 49 of end piece 47 located between the lens holder and the hinge 46. Because of the flexibility of the sideshield 18, the temple 14 as illustrated in FIG. 8 can be a spring-loaded temple at hinge 46, as is well known in the art. Thus, according to one embodiment, the temples can move outwardly in a direction away from each other as shown by arrow 74 a predetermined distance such as, for example only, approximately five degrees. Thus, eyeglasses with spring-loaded temples can be accommodated with the present device.

As discussed above, it can be seen in FIG. 1 that sideshields 16 and 18 are mirror images of each other, and thus only one sideshield has been disclosed and discussed in detail in the FIGS.

Figure 12:
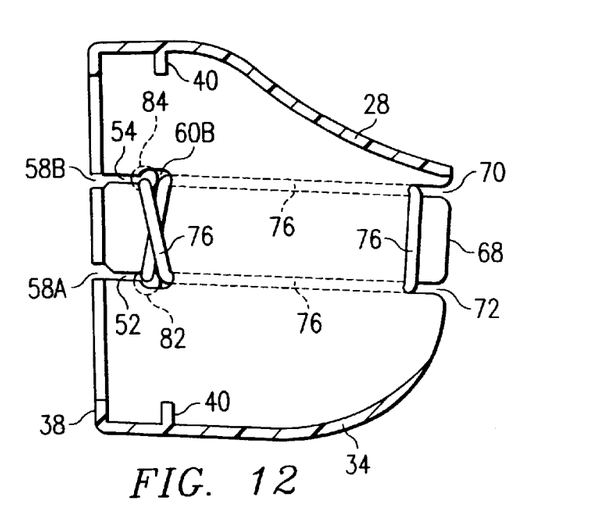
FIG. 12 is a side view of the sideshield prior to being attached to the eyeglass temple frames according to a second embodiment utilizing an elongated elastic member with bosses at each end.
Figure 13:
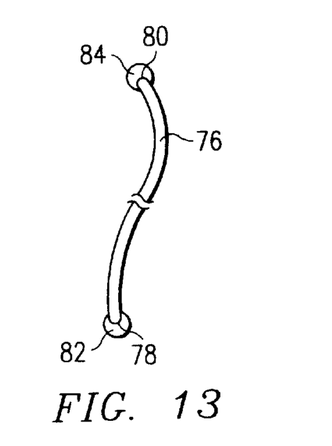
FIG. 13 illustrates the elongated elastic member having bosses at each end of FIG. 12.

FIG. 12 shows an embodiment similar to that of FIGS. 2 and 8, but instead of using an elastic band or "O"-ring, the elastomeric member 50 is an elongated elastic member 76 having first and second ends 78 and 80 such as shown in FIG. 13. Each of the first and second ends 78 and 80 include an enlarged portion or bosses 82 and 84. Bosses 82 and 84 maintain or hold the ends of the elastic member in the second enlarged areas 60A and 60B of slots 52 and 54, respectively. The enlarged areas 60A and 60B may preferably be elongated as shown in FIG. 12 for this embodiment since both ends of the elongated elastic member 76 are received by each of the enlarged areas 60A and 60B.

Figure 14:
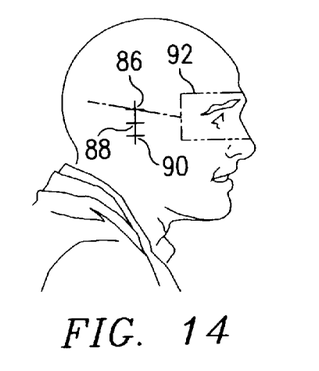
FIG. 14 is a side view of an outline of a human head illustrating in phantom lines the area to be protected by the full sideshield and also illustrating the different pantoscopic angles for various glasses.

FIG. 14 illustrates the different pantoscopic angles that can be found for various eyeglasses. Assuming that the eyeglass front portion 10 is vertically positioned in front of the eye, the temple could extend through either of the points 86, 88 or 90, thus varying the angle between the temple and the eyeglass lens in front of the eye. With the present invention, the pantoscopic angle can change as needed and the temple can extend through any of the points 86, 88 or 90 without affecting the attachment of the sideshield to the eyeglass front portion 10. FIG. 14 also illustrates in phantom lines the area 92 which is desired to be protected by the sideshields.

Figure 15:
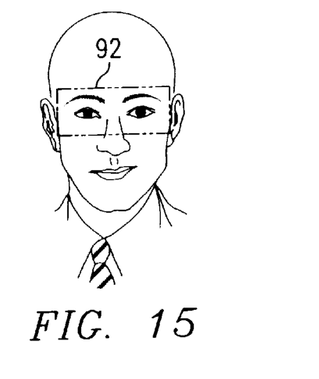
FIG. 15 is a front view of an illustration of a human head showing in phantom lines the area about the eyes protected by the sideshield of the present invention.

FIG. 15 is a front view of the representation of a face illustrating in phantom lines the area 74 about the eye that is protected by the novel sideshields of the present invention.

Thus, there has been disclosed a full sideshield for removable attachment to an eyeglass frame having a front and a rear and a pair of pivotally-mounted temples attached to corresponding mounting bracket projections or hinges extending from each side of the eyeglass frame for holding the eyeglass frame on the head of a user. The sideshield forms a semicircle around the eyeglass in front of the eye cavity of the user to provide at least partial protection on the top, bottom and side of the eye. The sideshield is generally arcuate-shaped and has a periphery for generally conforming to the shape of the eyeglass frame. The sideshield has a side portion 30 integrally framed along a first edge 32 with a top portion 28, and also integrally framed along a second edge 36 to a bottom portion 34. First and second flange portions 38 and 40 extend at least partially in front of and behind the eyeglass frame front portion to hold the eyeglass frame lens holder portions between the first and second flange portions 38 and 40. An elastomeric member 50 attaches the sideshield to the end piece or portion 47 of the eyeglass frame 10 between the side of lens holder and the hinge without interfering with movement of the temple.

The elastomeric member 50 may be a continuous elastic band 56 engaging the mounting bracket projection hinge or frame front 46 on the eyeglass frame front portion and extending into the enlarged areas 60A and 60B of first and second spaced slots 52 and 54 in the forward end of the sideshield and extending along the edges 32 and 36 joining the top portion 28 and bottom portion 34 to the side portion 30 into third and fourth spaced slots 72 and 74 at the opposite end or rear of the sideshield, and then under a substantially U-shaped tab or flange 68 such that, by stretching the continuous elastic band to engage the third and fourth slots and pass under the sideshield tab or flange 68, a tension is applied to the eyeglass frame and the sideshield to fixedly hold the sideshield to the eyeglass frame. Alternately, the elastomeric member 50 may be an elongated elastic member 76 with bosses 82 and 84 on each end to retain the member in the enlarged areas 60A and 60B of front slots 52 and 54.

Clearly, either the elongated elastic member 76 or the continuous elastic band 56 could be used to hold the sideshield to the eyeglass frame front portion.

The corresponding structures, materials, acts and equivalents of all means plus function elements in the claims below are intended to include any structure, material or act for performing the function in combination with other claimed elements as specifically claimed.

I claim:

1. A removable sideshield for use with an eyeglass frame having a pair of spaced eyeglass lens holders and a pair of temples attached by hinges to each side of said lens holders for holding the eyeglass frame on the head of the user, said sideshield providing protection at the top, bottom and side of the user's eye and comprising:

a generally arcuate-shaped shield member with a front and a rear and a periphery for generally conforming to the shape of the eyeglass lens holder and comprising a side portion integrally formed at a first edge to a top portion and integrally formed at a second edge to a bottom portion;

first and second enlarged slots formed in said front of said shield member having a first selected width, said first and second enlarged slots joining first and second spaced slots formed in said side portion of said shield member and having a second selected width which is less than said first selected width, each of said first and second spaced slots extending rearwardly proximate one of said first and second edges toward first and second enlarged areas, respectively;

a tab member defined by third and fourth spaced slots formed at said rear of said shield member; and an elastomeric member having a relaxed diameter greater than said second selected width of said first and second spaced slots such that said elastomeric member is deformed as it passes from said first and second enlarged slots through said first and second spaced slots into said first and second enlarged areas, said elastomeric member adapted to engage with a portion of said eyeglass frame between one of said spaced eyeglass lens holders and said hinge and extending into said first and second enlarged areas of said first and second spaced slots, and along said side portion of said shield member into said third and fourth spaced slots, and then passing under said tab member so as to thereby hold said sideshield on said eyeglass frame.

2. The apparatus of claim 1 wherein said elastomeric member is a continuous elastic band.

3. The apparatus of claim 1 wherein said elastomeric member is an elongated elastic member having first and second ends and having enlarged bosses at said first and second ends, said enlarged bosses having a diameter larger than said diameter of said first and second enlarged areas so as to retain said elongated elastic member in said enlarged areas.

4. The apparatus of claim 1 wherein said first and second enlarged areas have a diameter of about 0.10 inches, said first and second spaced slots have a width of about 0.03 inches and said elastic band has a relaxed diameter of about 0.070±0.01 inches.

5. The apparatus of claim 1 further comprising a first flange at said front of said shield member and extendable from at least one of said side portion, top portion and bottom portion of said shield member, and at least partially in front of and substantially parallel to said eyeglass lens holder.

6. The apparatus of claim 5 wherein said flange extends from each of said top portion, said side portion and said bottom portion.

7. The apparatus of claim 1 further comprising a "living hinge" extending a first selected distance proximate said first edge of said side portion and a second "living hinge" extending a second selected distance proximate said second edge of said side portion.

8. The apparatus of claim 7 wherein said removable sideshield has a nominal material thickness of about 0.050 inches, and said living hinges are grooves defined in said sideshield so as to leave a thickness of about 0.02 inches at said living hinge along said first edge and a thickness of about 0.03 inches at said living hinge along said second edge.

9. The apparatus of claim 5 wherein said first flange is extendable from substantially the entire periphery of the sideshield in font of the eyeglass lens holder.

10. The apparatus of claim 5 further comprising a second flange extending from the top and bottom portions of said shield member behind said eyeglass lens holder and substantially parallel to said first flange to secure said eyeglass lens holder between said first flange and said second flange.

11. The apparatus of claim 1 wherein a sideshield for one side of said eyeglass frame is the mirror image of the other side.

12. The apparatus of claim 1 wherein said arcuate-shaped shield member is made of polycarbonate.

13. The apparatus of claim 1 wherein said arcuate-shaped shield member is transparent.

14. The apparatus of claim 12 wherein said arcuate-shaped shield member is transparent.

15. A removable sideshield for use with an eyeglass frame having a pair of spaced eyeglass lens holders and a pair of temples attached by hinges to each side of said lens holders for holding the eyeglass frame on the head of the user, said sideshield providing protection at the top, bottom and side of the user's eye, said sideshield comprising:

a generally arcuate-shaped shield member with a front and a rear and a periphery for generally conforming to the shape of the eyeglass lens holder and comprising a side portion integrally formed at a first edge to a top portion and integrally formed at a second edge to a bottom portion;

first and second spaced slots formed in said side portion of said sideshield and each of said first and second spaced slots extending rearwardly from said front of said shield member proximate said first and second edges to first and second enlarged areas;

a tab member defined by third and fourth spaced slots formed at said rear of said shield member;

said side portion defining a first groove extending proximate said first edge at least part way between said first enlarged area and said third slot to form a first living hinge, and defining a second groove extending proximate said second edge at least part way between said second enlarged area and said fourth slot to form a second living hinge; and elastomeric member adapted to engage with a portion of said eyeglass frame between one of said spaced eyeglass lens holders and said hinge and extending from said first and second enlarged areas, proximate said first and second edges of said side portion into said third and fourth spaced slots, and then passing under said tab member to hold said sideshield on said eyeglass lens holder.

16. The apparatus of claim 15 further comprising a first flange at said front of said shield member and extending from at least one of said side portion, top portion and bottom portion of said shield member, and at least partially in front of and substantially parallel to said eyeglass lens holder.

17. The apparatus of claim 15 wherein said elastomeric member is a continuous elastic band.

18. The apparatus of claim 15 wherein said elastomeric member is an elongated elastic member having first and second ends and having enlarged bosses at said first and second ends, said enlarged bosses having a diameter larger than said diameter of said first and second enlarged areas so as to retain said elongated elastic member in said enlarged areas.

19. The apparatus of claim 15 further comprising a first flange extendable from substantially the entire periphery of the sideshield in front of the eyeglass lens holder.

20. The apparatus of claim 15 further comprising a second flange extending only from the top and bottom portions of said shield member behind said eyeglass lens holder and substantially parallel to said first flange to secure said eyeglass lens holder between said first flange and said second flange.

21. The apparatus of claim 15 wherein a sideshield for one side of said eyeglass frame is the mirror image of the other side.

22. The apparatus of claim 15 wherein said arcuate-shaped shield member is made of polycarbonate.

23. The apparatus of claim 15 wherein said arcuate-shaped shield member is transparent.

24. The apparatus of claim 22 wherein said arcuate-shaped shield member is transparent.

* * * * *